United States Patent
Mishima et al.

Patent Number: 5,885,267
Date of Patent: Mar. 23, 1999

[54] DISPOSABLE BODY FLUIDS ABSORBENT ARTICLE

[75] Inventors: Yoshitaka Mishima; Hideaki Kitaoka; Shingo Shimizu, all of Kagawa-ken, Japan

[73] Assignee: Uni-Charm Corporation, Ehime-ken, Japan

[21] Appl. No.: 882,786

[22] Filed: Jun. 26, 1997

[30] Foreign Application Priority Data

Jun. 28, 1996 [JP] Japan ..................... 8-170408

[51] Int. Cl.$^6$ .......................................... A61F 13/15
[52] U.S. Cl. ........................... 604/378; 604/385.1
[58] Field of Search .................... 604/378–380, 604/383, 385.1

[56] References Cited

U.S. PATENT DOCUMENTS 5,437,653  8/1995  Gilman et al. ..................... 604/378
5,486,167  1/1996  Dragoo et al. ..................... 604/384

FOREIGN PATENT DOCUMENTS 61-176346  8/1986  Japan.

Primary Examiner—John G. Weiss
Assistant Examiner—Dennis Ruhl
Attorney, Agent, or Firm—Lowe Hauptman Gopstein Gilman & Berner

[57] ABSTRACT

A disposable body fluids absorbent article including a liquid-permeable topsheet 2, a liquid-impermeable backsheet and a liquid-absorbent core 4 disposed therebetween. The topsheet includes a hydrophobic first fibrous layer made of thermally meltable synthetic fibers having a fineness of 0.02~0.04 d, a hydrophobic second fibrous layer underlying the first fibrous layer and made of thermoplastic synthetic fibers and having a fineness of 1.0~2.5 d and a hydrophilic third fibrous layer underlying the second fibrous layer and made of thermally meltable synthetic fibers and having a fineness of 3~6 d. A plurality of hollows extend through the first and second fibrous layers so that these hollows are closed by the third fibrous layer so as to form a plurality of recesses.

7 Claims, 1 Drawing Sheet

DISPOSABLE BODY FLUIDS ABSORBENT ARTICLE

BACKGROUND OF THE INVENTION

This invention relates generally to disposable body fluids absorbent articles and more particularly to disposable diapers, sanitary napkins, incontinent pads and the like.

It is well known to employ a topsheet having a plurality of openings in the above-mentioned articles For example, a body fluids absorbent article topsheet disclosed in Japanese Laid-Open Patent Application No. Sho-61176346 comprises a nonwoven fabric provided with a plurality of openings This nonwoven fabric is made of thermally meltable fibers each being as fine as less than 10 μm (approximately 0.04 d). The open area ratio of the topsheet openings as a whole is 10–50% and the minimum diameter of each opening is 0.3–2 mm. These openings are formed by subjecting a fibrous web placed on support means to high pressure water jets or by driving heated projections into the nonwoven fabric.

The above-cited Application also discloses that a fibrous layer made of hydrophilic fibers may be bonded to a lower side of the topsheet made of hydrophobic fibers.

The thermally meltable fibers having a fiber diameter leas than 10 μm and the nonwoven fabric made of such fibers are commonly known as melt-blown fibers and melt-blown nonwoven fabric, respectively. The melt-blown fibers are extremely soft and therefore the nonwoven fabric made of such fibers is suitable as the topsheet of the absorbent article because of its soft touch, However, such fibers have poor rigidity and it is difficult for the nonwoven fabric made of such fibers to provide both a desired bulk and cushioning effect. Accordingly, even if such a nonwoven fabric is employed as the topsheet of the absorbent article, it will be difficult for the topsheet to make the best use of the soft touch peculiar to this nonwoven fabric unless the fibrous layer selected to be bonded to the lower surface of this topsheet and the fibers selected to form a liquid-absorbent core of the article which comes in close contact with the topsheet have an adequate cushioning effect. As one of the measures to obtain such a cushioning effect, it may be contemplated to bond synthetic fibers having a fineness of 3 d or larger to the lower surface of the topsheet. However, the surface of the melt-blown nonwoven fabric is, in general, insufficiently fluffy to be reliably intertwined with fibers of such large fineness. While this problem may be solved by using a large amount of adhesive or by subjecting the topsheet and the underlying web to embossing at a high temperature under a high pressure, such treatment also will cause the feeling of the topsheet to be deteriorated.

SUMMARY OF THE INVENTION

In view of the problem described above, it is a principal object of the invention to allow a topsheet of body fluids absorbent article employing extremely fine synthetic fibers to provide a soft touch combined with a high cushioning effect.

The object set forth above is achieved, according to the invention, by a disposable body fluids absorbent article including a liquid-permeable topsheet on a skin-contactable side, a liquid-impermeable backsheet on a non-skin contactable side and a liquid-absorbent core disposed there between.

The topsheet comprises a hydrophobic first fibrous layer made of thermally meltable synthetic fibers having a fineness of 0.02–0.04 d, a hydrophobic second fibrous layer underlying the first fibrous layer and made of thermoplastic synthetic fibers having a fineness of 1.0 –2.5 d, and a hydrophilic third fibrous layer underlying the second fibrous layer and made of thermally meltable synthetic fibers having a fineness of 3–6 d. An upper surface of the first fibrous layer comprises a substantially liquid-impermeable skin-contactable region formed by the synthetic fibers accumulated at a relatively high density and liquid-permeable open regions each having an area of 1.0–2.0 mm$^2$ practically or completely without the synthetic fibers. A plurality of hollows extend downward from the open regions through the first and second fibrous layers to the third fibrous layer so that these hollows are closed by the third fibrous layer to form a plurality of recesses. The first, second and third fibrous layers are integrally laminated by the individual fibers of the respective fibrous layers bonded together along interfaces of these layers, In another aspect of the invention, the first and second fibrous layers have the individual fibers thereof mechanically intertwined and fused together along the interface of these layers.

In another aspect of the invention, each of the first, second and third fibrous layers has a fiber density of 5–40 g/m$^2$, respectively.

In another aspect of the invention, the open regions have an open area ratio of 10–50%.

In another aspect of the invention, the individual fibers of the first fibrous layer and/or the second fibrous layer extend circumferentially along peripheral edges of the open regions.

In another aspect of the invention, the individual fibers of the second fibrous layer are in a crimped state.

In yet another aspect of the invention, the individual fibers of the second and third fibrous layers are in a crimped state.

Other and further objects, features and advantages of the invention will appear more fully from the following description.

DESCRIPTION OF THE PREFERRED EMBODIMENT

Figure 1:
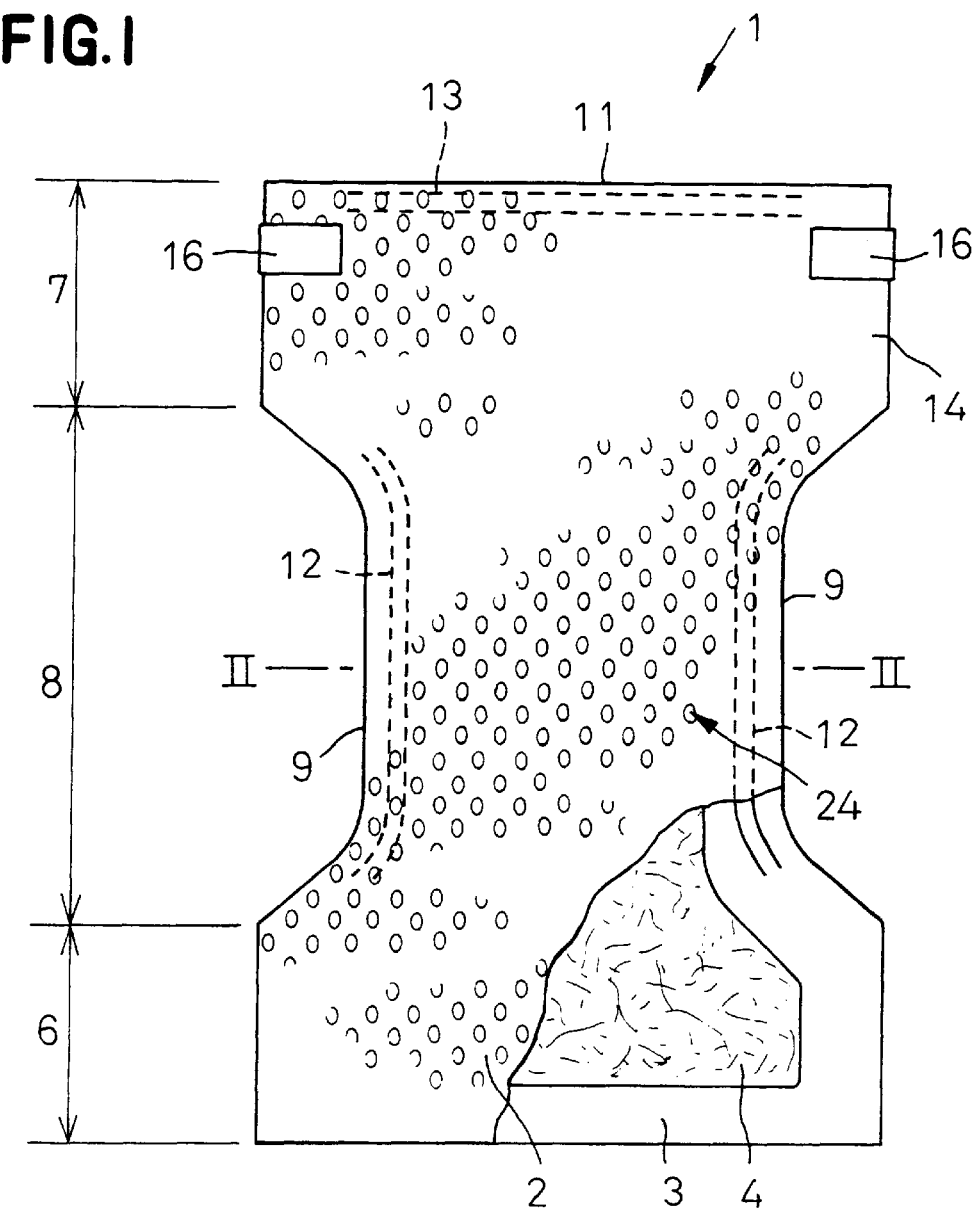
FIG. 1 is a plan view showing a disposable diaper as an embodiment of the invention as partially broken away.

A diaper 1 shown by FIG. 1 in a plan view as partially broken away comprises a liquid-permeable topsheet 2% a liquid-impermeable backsheet 3 and a liquid-absorbent core 4 extending therebetween to form a front waist region 6, a rear waist region 7 and a crotch region 8 between these two regions. Transversely opposite side edges of the crotch region 8 are inwardly curved to define peripheral edges 9 of respective leg-openings. The topsheet 2 and the backsheet 3 are bonded together at portions thereof extending outward beyond a peripheral edge of the absorbent core 4. The peripheral edges 9 of the respective leg-openings and a longitudinal end 11 of the rear waist region 7 are provided with elastic members 12 adapted to fit the diaper I around the wearer's legs and an elastic member 13 adapted to fit the diaper 1 along the waist of the wearer, These elastic members 12, 13 are secured in elastically stretched conditions to an inner surface of at least one of the topsheet 2 and the backsheet 3. A tape fastener 16 is attached to each of transversely opposite side edges 14 of the rear waist region 14.

Figure 2:
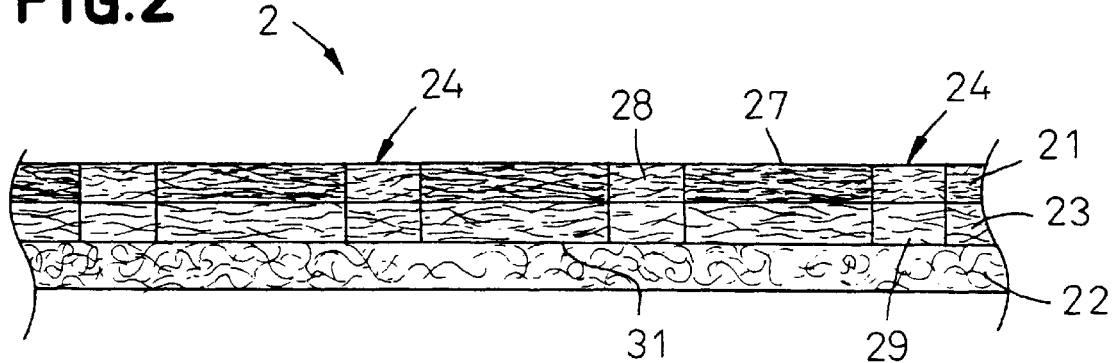
FIG. 2 is a sectional view showing a topsheet of the diaper taken along line II—II in FIG. 1

FIG. 2 is a sectional view showing the topsheet 2 taken along line II—II in FIG. 1. The topsheet 2 structurally comprises a top layer 21 adapted to contact with the wearer's skin, a bottom layer 22 overlying the absorbent core 4 and an intermediate layer 23 interposed between the top an bottom layers 21, 22. A plurality of openings 24 extend through both top layer 21 and intermediate layer 23 so that the bottom layer 22 closes these openings 24 and thereby forms a plurality of recesses.

The top layer 21 comprises a hydrophobic melt-blown nonwoven fabric formed by bonding melt-blown fibers of polypropylene having a fineness of 0.02–0.04 d. The to layer 21 has a fiber density of 5–40 g/m².

The intermediate layer 23 comprises a hydrophobic web made of core-sheath type composite fibers of polypropylene/polyethylene having a fineness of 1.0–2.5 d. The intermediate layer 23 has a fiber density of 5–40 g/m².

The top layer 21 and the intermediate layer 23 are bonded together through mechanical intertwinement (entanglement) and/or fusion (weld) among individual fibers of these layers, The openings 24 extending through these layers 21, 23 have top openings 28 in an upper surface (skin-contactable surface) 27 of the top layer 21 and bottom openings 29 in a lower surface of the intermediate layer 23. Each of the top openings 28 has an open area of 1.0–2.0 m, preferably 1.3–1.8 mm² and the top openings 28 as a whole have an open area ratio of 10–50%, preferably 15–30%, of the entire upper surface 27. Each of the bottom openings 29 has an open area of 50–120%, preferably 70–100% of the top opening 28.

The bottom layer 22 comprises a hydrophilic web made of core-sheath type composite fibers of polypropylene/polyethylene having a fineness of 3–8 d, preferably 3–6 d. The bottom layer 22 has a fiber density of 5–40 g/m².

The bottom layer 22 and the intermediate layer 23 are bonded together by fusing (welding) the individual fibers of these layers.

The topsheet 2 structurally composed as described above is placed upon the absorbent core 4 with the bottom layer 22 closely in contact with a skin-facing side of the absorbent core 4. If tissue paper or the like is used as a layer covering the absorbent core 4, it is preferable that the bottom layer 22 is intermittently bonded to this tissue paper by suitable means such as hot melt adhesive.

With the diaper 1 put on the wearer, the top layer 21 of the topsheet 2 advantageously provides a soft touch peculiar to the fibers of a relatively small fineness. The bottom layer 22, on the other hand, advantageously provides elasticity and a feeling of well-fitting. Urine discharged on the diaper 1 is guided through the openings 24 to the bottom layer 22 and then absorbed by the absorbent core 4. Rewetting, i.e., a phenomenon that a quantity of urine once absorbed by the absorbent core 4 flows back toward the wearer's skin, is reliably prevented by the hydrophobic top and intermediate layers 21, 23.

The melt-blown nonwoven fabric forming the top layer 21 is not a suitable means to keep the wearer's skin spaced apart from the bottom layer 22 as well as from the absorbent core 4 which are wetted with urine, since such nonwoven fabric is composed of the individual fibers which are poor not only their fineness but also their rigidity and tends to become excessively thin However, the topsheet 2 of this diaper 1 includes the intermediate layer 23 bonded to the lower surface of the top layer 21, which is hydrophobic and made of the fibers having a fineness larger than the fineness of individual fibers in the top layer 21. The problem which might occur when the top layer 21 alone is used is reliably compensated for by the intermediate layer 23 which is hydrophobic and relatively thick. In this manner, the wearer's skin is easily kept spaced apart from the wet absorbent core 4. While it will be possible to thicken the melt-blown nonwoven fabric forming the top layer 21 instead of using the intermediate layer 23, such countermeasure requires a cost substantially higher than when the intermediate layer 23 is used with the top layer 21 and is therefore not practical, since the intermediate layer 23 comprises a relatively bulky fiber web which can be easily produced by machines such as a comber or card. The intermediate layer 23 preferably has a relatively high fiber density and sufficiently large surface areas bonded to the top and bottom layers 21, 22. To achieve this, the fibers of a fineness smaller than that in the bottom layer 22 are used for the intermediate layer 23. Both the top layer 21 and the bottom layer 22 have a relatively large fineness and relatively high rigidity, so it will be difficult to bond these two layers directly to each other. The interposition of the intermediate layer 23 between these top and bottom layers 21, 22 facilitates lamination of these two layers. To bond the individual fibers of the respective layers 21, 22, 23 to one another, these fibrous layers put one upon another may be heated so as to fuse (weld) the individual fibers to one another, or subjected to high pressure water jets to achieve the desired mechanical intertwinement (entanglement) among the individual fibers. It will also be effective to treat the fibrous layers to a set of heat embossing rollers In the diaper shown by FIG. 1, the bottom layer 22 may be intermittently fusion-bonded to the intermediate layer 23 at a plurality of spots. These spots may be dimensioned to have a diameter of 1–2 mm, respectively, and arranged at regular intervals of approximately 10 mm adjacent the longitudinally opposite ends of the front and rear waist regions 6, 7 and at regular intervals of approximately 18 mm in the crotch region 8. The interval of the spots is relatively larger in order to avoid a problem that crowded spots might make the topsheet 2 hard and thereby deteriorate the feeling to wear the diaper 1.

The individual fibers of the top, bottom and intermediate layers 21, 22, 23 are not limited to those as have been described in reference with the illustrated embodiment and those of any other types which are well known or usually employed in this technical field may be also employed. For example, crimped fibers may be employed for the bottom layer 22 and the intermediate layer 23 to improve a cushioning effect of the bottom layer 22 and simultaneously to increase a thickness of the intermediate layer 23

The entire disclosure of Japanese Patent Application No. 8-170408 filed on Jun. 28, 1997 including specification, claims, drawings and abstract are incorporated herein by reference in its entirety.

Having described the invention as related to the embodiment shown in the accompanying drawings, it is our intention that the invention be not limited by any of the details of description, unless otherwise specified, but rather be construed broadly within its spirit and scope as set out in the accompanying claims.

What is claimed is:

1. A disposable body fluids absorbent article including a liquid-permeable topsheet on a skin-contactable side, a liquid-impermeable backsheet on a non-skin-contactable side and a liquid-absorbent core disposed therebetween, wherein:

said topsheet comprises a hydrophobic first fibrous layer made of polypropylene fibers having a fineness of 0.02~0.04 d, a hydrophobic second fibrous layer underlying said first fibrous layer and made of core-sheath type composite fibers of polypropylene/polyethylene and having a fineness of 1.0~2.5 d and a hydrophilic third fibrous layer underlying said second fibrous layer and made of core-sheath type composite fibers of polypropylene/polyethylene and having a fineness of 3~6 d;

an upper surface of said first fibrous layer comprises a substantially liquid-impermeable skin-contactable region formed by said polypropylene fibers accumulated at a relatively high density and liquid-permeable open regions each having an area of 1.0~2.0 mm$^2$ formed substantially entirely without said synthetic fibers, and a plurality of openings extend downward from said open regions through said first and second fibrous layers to said third fibrous layer and are closed by said third fibrous layer so as to form a plurality of recesses; and wherein said first, second and third fibrous layers are integrally laminated by the individual fibers of the respective layers bonded together along interfaces of these layers.

2. The article according to claim 1, wherein said first and second fibrous layers have individual fibers thereof mechanically intertwined and fused together along the interface of these layers.

3. The article according to claim 1 wherein each of said first, second and third fibrous layers has a fiber density of 5–40 g/m$^2$.

4. The article according to claim 1 wherein said open regions have an open area ratio of 10–50% to said topsheet.

5. The article according to claim 1 wherein the individual fibers of at least one of said first fibrous layer and said second fibrous layer extend circumferentially along peripheral edges of said open regions.

6. The article according to claim 1 wherein the individual fibers of said second fibrous layer are in a crimped state.

7. The article according to claim 1 wherein the individual fibers of said second and third fibrous layers are in a crimped state.

* * * * *